US012635895B2

(12) United States Patent
Clark et al.

(10) Patent No.:  US 12,635,895 B2
(45) Date of Patent:      May 26, 2026

(54) SYSTEMS AND METHODS FOR MONITORING INTRACRANIAL COMPLIANCE

(71) Applicant: UNIVERSITY OF PITTSBURGH-OF THE COMMONWEALTH SYSTEM OF HIGHER EDUCATION, Pittsburgh, PA (US)

(72) Inventors: Robert Clark, Pittsburgh, PA (US); Gilles Clermont, Fombell, PA (US); Michael Wolf, Nashville, TN (US)

(73) Assignee: UNIVERSITY OF PITTSBURGH-OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 916 days.

(21) Appl. No.: 17/524,791

(22) Filed: Nov. 12, 2021

(65) Prior Publication Data

US 2022/0071501 A1      Mar. 10, 2022

Related U.S. Application Data

(63) Continuation of application No. PCT/US2020/025932, filed on Mar. 31, 2020.
(Continued)

(51) Int. Cl.
*A61B 5/03*          (2006.01)
*A61B 5/00*          (2006.01)
(Continued)

(52) U.S. Cl.
CPC ............ *A61B 5/031* (2013.01); *A61B 5/6868* (2013.01); *A61B 5/746* (2013.01); *A61B 2562/0247* (2013.01)

(58) Field of Classification Search
CPC ....... A61B 5/031; A61B 5/6868; A61B 5/746; A61B 2562/0247; A61B 5/7282;
(Continued)

(56) References Cited

U.S. PATENT DOCUMENTS

| | | |
|---|---|---|
| 4,893,630 A | 1/1990 | Bray, Jr. |
| 7,547,283 B2 | 6/2009 | Mourad et al. |

(Continued)

FOREIGN PATENT DOCUMENTS

| | | |
|---|---|---|
| CA | 2 775 675 A1 | 5/2010 |
| WO | WO 2016/164891 A1 | 10/2016 |

OTHER PUBLICATIONS

Codman case study (Year: 2021).*
(Continued)

*Primary Examiner* — Justin Xu
(74) *Attorney, Agent, or Firm* — Baker Botts L.L.P.

(57) ABSTRACT

System for monitoring intracranial compliance in a patient includes an intracranial pressure sensor, configured to obtain a measurement indicative of an intracranial pressure of a patient, a $CO_2$ sensor, configured to obtain a measurement indicative of a $CO_2$ level of the patient, and a processor, configured to determine an intracranial compliance from the measurements indicative of the intracranial pressure and the $CO_2$ level. Methods for monitoring intracranial compliance in a patient are also provided.

8 Claims, 17 Drawing Sheets

Related U.S. Application Data

(60) Provisional application No. 62/848,966, filed on May 16, 2019.

(51) Int. Cl.

| | |
|---|---|
| *A61B 5/083* | (2006.01) |
| *A61B 5/05* | (2021.01) |
| *A61B 5/24* | (2021.01) |

(58) Field of Classification Search
CPC ... A61B 5/0836; A61B 5/7246; A61B 5/7285; A61B 5/05; A61B 5/24; A61B 5/4064
See application file for complete search history.

(56) References Cited

U.S. PATENT DOCUMENTS

| | | | |
|---|---|---|---|
| 8,556,811 B2 | 10/2013 | Brady | |
| 2002/0128569 A1 | 9/2002 | Collins | |
| 2007/0066915 A1 | 3/2007 | Frei et al. | |
| 2010/0010322 A1* | 1/2010 | Brady | A61B 5/02028 |
| | | | 600/301 |
| 2010/0049082 A1* | 2/2010 | Hu | A61B 5/031 |
| | | | 600/561 |
| 2013/0109979 A1 | 5/2013 | Poupko et al. | |
| 2014/0073937 A1* | 3/2014 | Rodriguez-Llorente | A61B 5/7246 |
| | | | 600/476 |
| 2014/0316218 A1* | 10/2014 | Purdon | A61B 5/369 |
| | | | 600/301 |
| 2014/0371545 A1 | 12/2014 | Ben-Ari et al. | |
| 2016/0018846 A1 | 1/2016 | Zenoff | |
| 2016/0162786 A1* | 6/2016 | Grudic | G06N 7/01 |
| | | | 706/50 |
| 2018/0249920 A1 | 9/2018 | Hughes et al. | |
| 2020/0237977 A1* | 7/2020 | Panotopoulos | A61M 1/77 |
| 2021/0251546 A1* | 8/2021 | Tai | A61B 5/4064 |

OTHER PUBLICATIONS

Phillips CO2 Solutions Quick Start Guide (Year: 2010).*
StackOverflow forum question (Year: 2017).*
International Search Report mailed Jul. 1, 2020 in International Application No. PCT/US20/25932.
Ursino et al., "Interaction among autoregulation, CO2 reactivity, and intracranial pressure: a mathematical model," Jan. 28, 1998, 14 pgs. [online] retrieved from < URL: https://journals.physiology.org/doi/pdf/10.1152/ajpheart.1998.274.5.H1715 >.
Clarke, "The effects of inverse ratio ventilation on intracranial pressure: a preliminary report," Intensive Care Medicine, 23:106-109 (1997).
Extended European Search Report dated Sep. 15, 2023 in Application No. EP 20806294.
Wolf et al., "Assessment of Dynamic Intracranial Compliance in Children with Severe Traumatic Brain Injury: Proof-of-Concept," Neurocritical Care, 34:209-217 (2021).

* cited by examiner

Patient 2: Abnormal Intracranial Compliance 1-hour average of 10-minute correlation between ETCO2 and ICP 10-minute-averaged ETCO2 and ICP Patient 1: Normal Intracranial Compliance 1-hour average of 10-minute correlation between ETCO2 and ICP 10-minute-averaged ETCO2 and ICP $$Intracranial\ Compliance = \frac{\sum_{i=1}^{n}(X_{a,i}-\bar{X}_a)(Y_{b,i}-\bar{Y}_b)}{\sqrt{\sum_{i=1}^{n}(X_{a,i}-\bar{X}_a)^2\sum_{j=1}^{n}(Y_{b,j}-\bar{Y}_b)^2}}$$

Patient 1

Patient 2

Patient 3

Patient 4

A   No Decompressive Craniotomy/Craniectomy

SYSTEMS AND METHODS FOR MONITORING INTRACRANIAL COMPLIANCE

CROSS REFERENCE TO RELATED APPLICATION

This application is a continuation of International Patent Application No. PCT/US2020/025932, filed Mar. 31, 2020, which claims priority to U.S. Provisional Patent Application No. 62/848,966, filed May 16, 2019, the contents of which are hereby incorporated by reference in their entireties.

STATEMENT REGARDING FEDERALLY-SPONSORED RESEARCH

This invention was made with government support under Grant No. HD040686 awarded by the National Institutes of Health. The government has certain rights in the invention.

BACKGROUND

Standard of care neurological monitoring can include, for example and without limitation, intracranial pressure monitoring. Such techniques can allow a clinician to provide therapies on a reactionary basis, for example in response to intracranial hypertension that can be identified from spikes in intracranial pressure, or on an empirical basis. However, these techniques can be insufficient for reducing high rates of neurological morbidity and mortality.

Assessment of intracranial compliance can provide insight into the brain's capacity to tolerate abrupt physiologic changes and its responses to therapeutic interventions. Existing techniques for measuring intracranial compliance can involve a separate mechanical device to be inserted into the brain, for example through an additional hole in the skull. These techniques can also involve manipulation of intracranial volume to provoke changes in intracranial pressure, for example using an inflatable air-filled balloon in a closed system, or injecting a known volume of saline into the brain via an external ventricular drain to obtain a resultant change in intracranial pressure. These techniques thus can lead to intracranial hypertension, for example if compliance is poor. Furthermore, such techniques can lead to increased risk of infection and/or bleeding that can result from installation of separate, dedicated intracranial hardware.

Accordingly, there is an opportunity for improved techniques to monitor intracranial compliance that reduce or avoid the use of invasive procedures and/or devices. It can also be desirable for such techniques to permit proactive implementation and/or titration of medications or therapies, and thus improve the quality of neurological outcomes in patients.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a system for monitoring intracranial compliance in a patient, including an intracranial pressure sensor, a $CO_2$ sensor and a processor coupled to or in communication with the intracranial pressure sensor and the $CO_2$ sensor. The intracranial pressure sensor is configured to obtain a measurement indicative of an intracranial pressure of a patient. The $CO_2$ sensor is configured to obtain a measurement indicative of a $CO_2$ level of the patient. The processor is configured to determine an intracranial compliance from the measurements indicative of the intracranial pressure and the $CO_2$ level of the patient.

In addition or as a further alternative, as embodied herein, the intracranial pressure sensor can include a pressure sensor implanted in or disposed proximate a skull of the patient.

Additionally or alternatively, as embodied herein, the $CO_2$ sensor can include an end tidal $CO_2$ sensor or a partial pressure of $CO_2$ sensor.

Furthermore or as another alternative, as embodied herein, the processor can be configured to synchronize the measurements indicative of the intracranial pressure and the $CO_2$ level of the patient. The processor can be configured to determine a correlation coefficient from the measurements indicative of the intracranial pressure and the $CO_2$ level of the patient. The correlation coefficient can represent the intracranial compliance.

In addition or as a further alternative, the system can include a user interface. The processor can be configured to provide the intracranial compliance to the user interface. The user interface can include a monitor. The user interface can be configured to provide an alert when the intracranial compliance exceeds a threshold indicating abnormal compliance.

Additionally or alternatively, as embodied herein, the processor can be configured to provide the intracranial compliance to an electronic health record. The processor can be configured to determine a therapy based on the intracranial compliance. The processor can be configured to determine an updated intracranial compliance based on a change in at least one of the measurements indicative of the intracranial pressure and the $CO_2$ level of the patient in response to the therapy. The processor can be configured to predict a response of the patient to one or more determined therapies. The therapy can be selected based on the predicted response of the patient to the one or more determined therapies.

The disclosed subject matter also includes a method for monitoring intracranial compliance in a patient including obtaining a measurement indicative of an intracranial pressure of a patient, obtaining a measurement indicative of a $CO_2$ level of the patient, and determining an intracranial compliance from the measurements indicative of the intracranial pressure and the $CO_2$ level of the patient.

Additionally or alternatively, as embodied herein, the measurement indicative of the intracranial pressure can be obtained from a pressure sensor implanted in or disposed proximate a skull of the patient.

Furthermore or as another alternative, as embodied herein, the measurement indicative of the $CO_2$ level of the patient can include an end tidal $CO_2$ of the patient. Additionally or alternatively, the measurement indicative of the $CO_2$ level of the patient can include a partial pressure of $CO_2$ of the patient.

In addition or as a further alternative, at least one of the measurements indicative of the intracranial pressure and the $CO_2$ level of the patient can be obtained from a data acquisition platform. At least one of the measurements indicative of the intracranial pressure and the $CO_2$ level of the patient can be obtained from an electronic health record. At least one of the measurements indicative of the intracranial pressure and the $CO_2$ level of the patient can be obtained from a standard of care monitor for intensive care.

Additionally or alternatively, as embodied herein, the method can include synchronizing the measurements indicative of the intracranial pressure and the $CO_2$ level of the patient. The method can include determining a correlation coefficient from the measurements indicative of the intracranial pressure and the $CO_2$ level of the patient. The correlation coefficient can represent the intracranial compliance.

Furthermore or as another alternative, as embodied herein, the method can include at least one of providing the intracranial compliance to a user interface, providing an alert when the intracranial compliance exceeds a threshold indicating abnormal compliance, and providing the intracranial compliance to an electronic health record. The method can include determining a therapy based on the intracranial compliance. The method can include determining an updated intracranial compliance based on a change in at least one of the measurements indicative of the intracranial pressure and the $CO_2$ level of the patient in response to the therapy. The method can include predicting a response of the patient to one or more determined therapies. The therapy can be selected based on the predicted response of the patient to the one or more determined therapies.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

DETAILED DESCRIPTION

Figures 1, 2A:
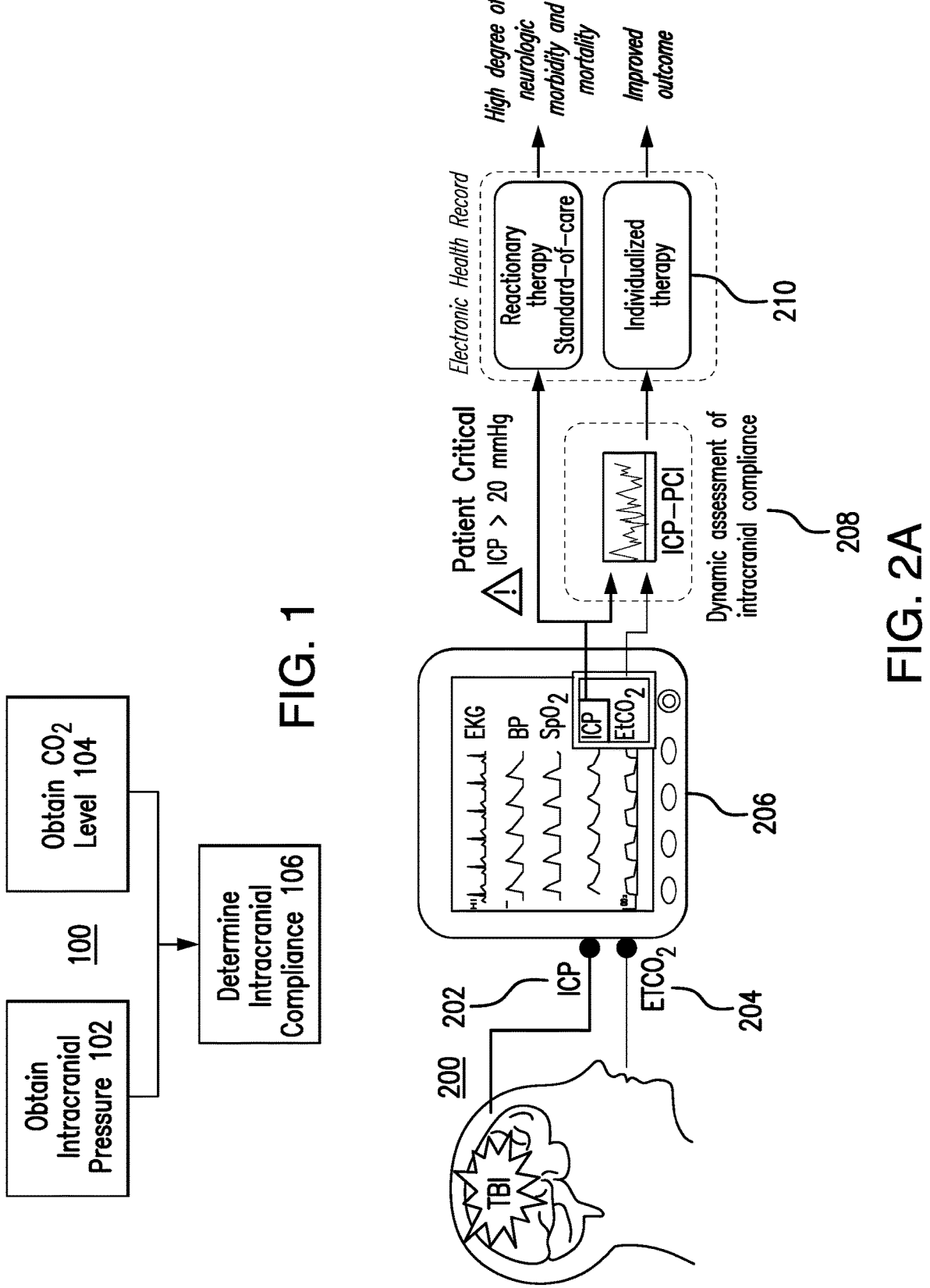
FIG. 1 is a block diagram illustrating an exemplary embodiment of a method for monitoring intracranial compliance in a patient in accordance with the disclosed subject matter.
FIG. 2A is a schematic diagram illustrating an exemplary embodiment of a system for monitoring intracranial compliance in a patient in accordance with the disclosed subject matter.

Reference will now be made in detail to the various embodiments of the disclosed subject matter, exemplary embodiments of which are illustrated in the accompanying drawings. The structure and corresponding method of operation of the disclosed subject matter will be described in conjunction with the detailed description of the system.

As used herein, the term "compliance" can refer to the relationship between changes in pressure and changes in volume of a material or component, which as embodied herein, can be an organ, including but not limited to the skull or the cranium. Compliance can be represented conceptually as the inverse of stiffness. Measurement of compliance can be valuable for understanding the physiology or pathophysiology of structures, including but not limited to blood vessels and heart chambers, as well as the intrathoracic and intracranial compartments. Knowledge of intracranial compliance (PCI), for example and without limitation, can be valuable for patients with or at risk for intracranial hypertension or elevated intracranial pressure (ICP). Management of ICP to suitable levels can improve outcomes for patients with a wide-range of conditions, including but not limited to, severe traumatic brain injury (TBI), intracranial hemorrhage (ICH), and acute hydrocephalus (AH).

The systems and methods described herein can, for example and without limitation, be incorporated into or utilize existing monitoring devices or techniques considered standard of care for neurointensive care patients to determine a PCI. Additionally or alternatively, the systems and methods described herein can be implemented as or involve the use of a separate, stand-alone system for monitoring PCI.

PCI can provide insight into the capacity of the brain to tolerate minute-to-minute physiologic changes in the brain's blood supply or cerebrospinal fluid volume, thereby improving a clinician's decision-making ability to add, adjust, and/or discontinue medicines/therapeutic interventions, and accordingly quality of care for patients requiring neurointensive care. For example, patients admitted to neurointensive care units can receive therapies such as osmotherapies, sedation and paralysis, blood pressure control, hyperventilation, temperature control, head-of-bed elevation, and CSF diversion. With standard of care neurological monitoring, administration of each of these therapies can be reactionary, for example in response to intracranial hypertension, and the patient's response to each of these therapies can thus be determined after the intervention is applied to the patient. Monitoring PCI, for example and without limitation, can allow a clinician to predict the patient's response to each of these therapies, thereby permitting individualized titration of medications or addition/removal of other therapies.

In accordance with the disclosed subject matter herein, systems for monitoring PCI in a patient generally include an intracranial pressure sensor, a $CO_2$ sensor and a processor coupled to or in communication with the intracranial pressure sensor and the $CO_2$ sensor. The intracranial pressure sensor is configured to obtain a measurement indicative of an intracranial pressure of the patient. The $CO_2$ sensor is configured to obtain a measurement indicative of a $CO_2$ level of the patient. The processor is configured to determine a PCI from the measurements indicative of the intracranial pressure and the $CO_2$ level of the patient.

In accordance with another aspect of the disclosed subject matter, methods for monitoring PCI in a patient are provided. Methods for monitoring PCI include obtaining a measurement indicative of an intracranial pressure of a patient, obtaining a measurement indicative of a $CO_2$ level of the patient, and determining a PCI from the measurements indicative of the intracranial pressure and the $CO_2$ level of the patient.

The accompanying figures, where like reference numerals refer to identical or functionally similar elements throughout the separate views, further illustrate various embodiments and explain various principles and advantages all in accordance with the disclosed subject matter. For purpose of explanation and illustration, and not limitation, exemplary embodiments of systems and methods for monitoring PCI in accordance with the disclosed subject matter are shown and described below.

FIG. 1 is a block diagram illustrating an exemplary method 100 for monitoring PCI in a patient in accordance with the disclosed subject matter. FIG. 2A is a schematic diagram illustrating an exemplary system 200 for monitoring PCI in a patient in accordance with the disclosed subject matter.

With reference to the exemplary method 100 of FIG. 1 in conjunction with the exemplary system 200 of FIG. 2A, at 102, a measurement indicative of an intracranial pressure (ICP) of a patient is obtained. For purpose of illustration and not limitation, as embodied herein, an intracranial pressure (ICP) of the patient can be obtained directly, for example and without limitation, using an intracranial pressure sensor 202, which, as embodied herein, can include a pressure sensor implanted in or disposed proximate the skull of the patient. Alternatively, ICP can be obtained from a data acquisition platform, such as and without limitation Bedmaster Ex (Excel Medical, Jupiter, FL), and/or to an electronic health record platform (e.g., by Cerner, Kansas City, MO; or Epic, Verona, WI), or any other suitable system or technique to obtain ICP information. As a further alternative, ICP can be obtained indirectly by a determination based on one or more other measurement, for example and without limitation by cerebral perfusion pressure ("CPP") and/or mean arterial pressure ("MAP"). As embodied herein, ICP can be obtained as a continuous measurement. Additionally or alternatively, estimations of continuous ICP can be obtained from existing, standard of care monitors for neurointensive care, or monitors in development for neurointensive care, including, but not limited to, measurements obtained from near infrared spectroscopy, ultrasonography, or pupillometry.

At 104, a measurement indicative of a level of carbon dioxide ($CO_2$) of the patient is obtained. For purpose of illustration and not limitation, the measurement can include a measurement indicative of a pressure or concentration of $CO_2$ of the patient. For example and without limitation, the measurement can include an end tidal $CO_2$ ($ETCO_2$) of the patient, which as embodied herein, can be obtained directly using $CO_2$ sensor 204. For example and not limitation, $CO_2$ sensor 204 can include an end tidal $CO_2$ sensor, which can be disposed in an endotracheal tube. Alternatively, a measurement indicative of a level of $CO_2$ of the patient can be obtained from a data acquisition platform, such as and without limitation Bedmaster Ex (Excel Medical, Jupiter, FL), and/or from an electronic health record platform (e.g., by Cerner, Kansas City, MO; or Epic, Verona, WI), or any other suitable system or technique to obtain $CO_2$ information. As embodied herein, the measurement indicative of a level of $CO_2$ can be obtained as a continuous measurement. Additionally or alternatively, the measurement indicative of the level of $CO_2$ of the patient can include a partial pressure of $CO_2$ ($PCO_2$), which can be obtained from existing, standard of care monitors for intensive care, or monitors in development for intensive care, including, but not limited to, measurements obtained from transcutaneous or indwelling vascular catheter sensors.

As embodied herein, intracranial pressure sensor 202 and $CO_2$ sensor 204 can be components of existing monitoring equipment considered standard of care for neurointensive care patients used to monitor the ICP and the $CO_2$ level of the patient, and such existing monitoring equipment can be configured to include or for use with system 200 for monitoring PCI. Alternatively, system 200, including intracranial pressure sensor 202 and $CO_2$ sensor 204, can be a separate, stand-alone system or module for monitoring PCI.

With continued reference to FIGS. 1 and 2A, at 106, a PCI of the patient is determined from the measurements indicative of the intracranial pressure and the $CO_2$ level of the patient. For purpose of illustration and not limitation, as embodied herein, a processor 208 can be configured to determine a PCI from the ICP and $ETCO_2$ of the patient. For example and not limitation, the processor 208 can be coupled to in communication with the intracranial pressure sensor 202 and the end tidal $CO_2$ sensor 204 such that the processor 208 can receive the ICP and $ETCO_2$ data from the intracranial pressure sensor 202 and the end tidal $CO_2$ sensor 204. For example, the processor 208 can use, or communicate locally or remotely with, a clinical monitoring program, such as the Bedmaster Ex, to obtain the ICP and $ETCO_2$ data. As embodied herein, the processor 208 can further synchronize measurements of the ICP and $ETCO_2$ data.

To determine the PCI, for purpose of illustration only and not limitation, the processor 208 can calculate a mean of and/or a change in each of the ICP and $ETCO_2$, and additionally or alternatively, their derivative signals, over physiologically relevant windows of time. The processor 208 can further compute a ratio of the mean of changes in each of the ICP and $ETCO_2$. The resulting ratio can represent the PCI over a certain window of time, which can represent a measure or estimate of instantaneous physiologic compliance. For example, and as embodied herein, a correlation coefficient of the ICP and $ETCO_2$ and the ratio can be compared using a calibration curve to determine the PCI. As embodied herein, the calibration can translate the numerical correspondence between the correlation of the ICP and $ETCO_2$ and ratios of their various derivatives, over selected windows of time. For purpose of illustration and not limitation, as embodied herein, the calibration curve can be determined from training data previously obtained from the patient, or from a population of patients, relating the correlation coefficient to PCI. Additionally or alternatively, and as embodied herein, the calibration curve can be determined or refined using statistical regression techniques.

As embodied herein, a higher correlation coefficient can indicate poor compliance, and a lower correlation coefficient indicates normal compliance. As embodied herein, the processor 208 can smooth the mean of each of the ICP and ETCO$_2$ with a computed moving average of the mean of each of the ICP and ETCO$_2$. The smoothing of the mean can omit values of the ICP and/or ETCO$_2$ that exceed the mean by a certain amount, for example and not limitation, at least fifty percent (50%). As embodied herein, the correlation coefficient can be calculated over five second intervals.

As embodied herein, the processor 208 can be configured using software, such as MATLAB, programmed to determine the PCI. For purpose of illustration only, and not limitation, vectors representing the mean of and change in each of the ICP and ETCO$_2$ can be rendered at five second intervals. The start of computation can be identified as an initial time in which both the ICP and ETCO$_2$ are available. Absent values at a given time point, which can represent monitor malfunction or disconnection, can be omitted. The five-second vectors can be converted or combined in to one-minute vectors. The one-minute vectors can then be formed into matrices with rows representing ten minutes of the ICP and ETCO$_2$. A correlation coefficient, which for example and as embodied herein can be a Pearson's coefficient, can be computed between each ten-minute row for the length of the ICP and ETCO$_2$ matrices to yield a vector of Pearson's correlations. The vector of Pearson's correlations can be smoothed by a computed moving average across a window, which can encompass, for example, the current data point and the five preceding points. The resulting smoothed vector can be an index representing the one-hour moving average of the ten-minute Pearson's correlation coefficient between the ICP and ETCO$_2$ or the change in the ICP and ETCO$_2$. The area under the curve of the resulting smoothed vector can be calculated for each hour of monitoring or more granular epochs and can be plotted against time. The resulting correlation plots can represent PCI.

The processor 208 can utilize additional or alternative techniques to determine PCI from measurements indicative of the ICP and the CO$_2$ level. For example and not limitation, vectors representing ICP and ETCO$_2$ data measured at 5-second intervals can be rendered. The start of computation can be identified as an initial time in which both the ICP and ETCO$_2$ are available. A vector tracking the time axis for each plot can be rendered. The ICP and ETCO$_2$ data can be filtered by omitting values that exceed a local mean, for example and not limitation, by at least fifty percent (50%). The ICP and ETCO$_2$ data can be placed into a matrix where each row represents one minute. The one-minute rows can be averaged to create smoothed ICP and ETCO$_2$ vectors. The smoothed ICP and ETCO$_2$ vectors can be plotted against time. The smoothed ICP and ETCO$_2$ vectors can be offset in time by one or more lag factors, and can be used to calculate a global correlation between ICP and ETCO$_2$ for each lag factor. The global correlation can be plotted for each lag factor to determine a peak lag factor, which can be a lag at which the correlation between ICP and ETCO$_2$ is greatest. The peak lag factor can be applied to the smoothed ICP and ETCO$_2$ vectors. The smoothed ICP and ETCO$_2$ vectors can be divided into a matrix, in which each row can represent one hour. A vector representing the correlation coefficients between each pair of one-hour rows in the ICP and ETCO$_2$ matrices can be rendered. The correlation coefficient vector can be recalculated, for example and not limitation, each minute. The correlation coefficient vector can be plotted against time. The moving mean of the correlation coefficient vector can be computed over a ten-minute and one-hour window. The resulting plot of the correlation coefficient vector can represent the PCI.

With continued reference to FIG. 2A, the processor 208 can be coupled to or in communication with a user interface 210. The user interface can be a display or a monitor such that a clinician can view the PCI of the patient. For example, the PCI can be provided to a data acquisition platform, such as and without limitation Bedmaster Ex (Excel Medical, Jupiter, FL), and/or to an electronic health record platform (e.g., by Cerner, Kansas City, MO; or Epic, Verona, WI). Additionally or alternatively, the monitor can be a stand-alone bedside monitor, such as an existing bedside monitor suitable for neurocritical care.

Figure 2B:
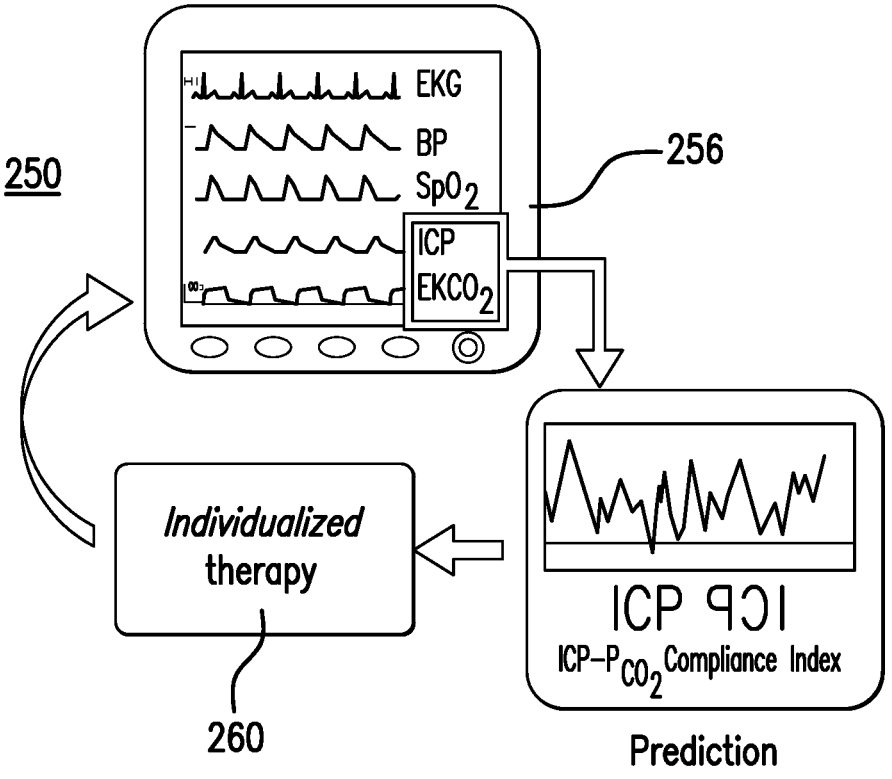
FIG. 2B is a schematic diagram illustrating an alternative embodiment of a system for monitoring intracranial compliance in a patient in accordance with the disclosed subject matter.

FIG. 2B is a schematic diagram illustrating an alternative embodiment of an exemplary system 250 for monitoring PCI in a patient in accordance with the disclosed subject matter. The system 250 can include a monitoring system 256, a processor 258, and a therapy module 260. For example and not limitation, the processor 258 can be coupled to in communication with the monitoring system 256 to receive ICP and ETCO$_2$ data obtained by the monitoring system 256 as described herein. The processor 258 can be configured to determine a PCI from the ICP and ETCO$_2$ data using any of the techniques described herein. The therapy module 260 can be coupled to or in communication with the processor 258 to receive the PCI of the patient.

For purpose of illustration and not limitation, as embodied herein, the therapy module 260 can determine an individualized therapy based on the PCI. For example and not limitation, therapy module 260 can evaluate one or more therapies appropriate to relieve traumatic brain injury or related systems based on the PCI, which can include information or analysis regarding how the therapy would affect PCI. As embodied herein, therapy module 260 can suggest one or more therapies to traumatic brain injury relieve traumatic brain injury or related systems based at least in part on how the therapy would affect PCI. For example and not limitation, the therapy module 260 can suggest initiation of one or more therapies to target abnormal PCI, including, but not limited to, hyperosmolar therapies such as hypertonic saline, or mannitol; use of sedative medications such as opioids, barbiturates, benzodiazepines, Propofol, or ketamine; drug-induced coma; therapeutic hypothermia; modification of minute ventilation CO$_2$ target; modification of blood pressure target; diversion of cerebrospinal fluid; or surgical decompression.

Additionally or alternatively, and as embodied herein, the therapy module 260 can display suggested therapies to a clinician or can initiate a therapy to the patient, as appropriate. The therapy module 260 can also provide feedback to the monitoring system 256, for example to update measurements of ICP and ETCO$_2$ data, and/or to instruct processor 258 to receive updated ICP and ETCO$_2$ data from the monitoring system 256 and determine an updated PCI. The clinician can observe the updated PCI and can, or can instruct therapy module 260 to, continue, change or cease the therapy. For example and not limitation, the therapy module 260 can suggest addition of one or more therapies to target the updated PCI, including, but not limited to, hyperosmolar therapies, use of sedative medications, drug-induced coma, therapeutic hypothermia, modification of minute ventilation CO$_2$ target, modification of blood pressure target, diversion of cerebrospinal fluid, or surgical decompression.

Furthermore or as further alternatives, for example and not limitation, therapy module 260 can suggest titration of one or more therapies to target updated PCI, including, but not limited to, hyperosmolar therapies, use of sedative medications, drug-induced coma, therapeutic hypothermia, modification of minute ventilation $CO_2$ target, modification of blood pressure target, diversion of cerebrospinal fluid, or surgical decompression. For example and not limitation, therapy module 260 can suggest discontinuation of one or more therapies upon normalization of PCI, including, but not limited to, hyperosmolar therapies, use of sedative medications, drug-induced coma, therapeutic hypothermia, modification of minute ventilation $CO_2$ target, modification of blood pressure target, diversion of cerebrospinal fluid, or surgical decompression.

Figure 3:
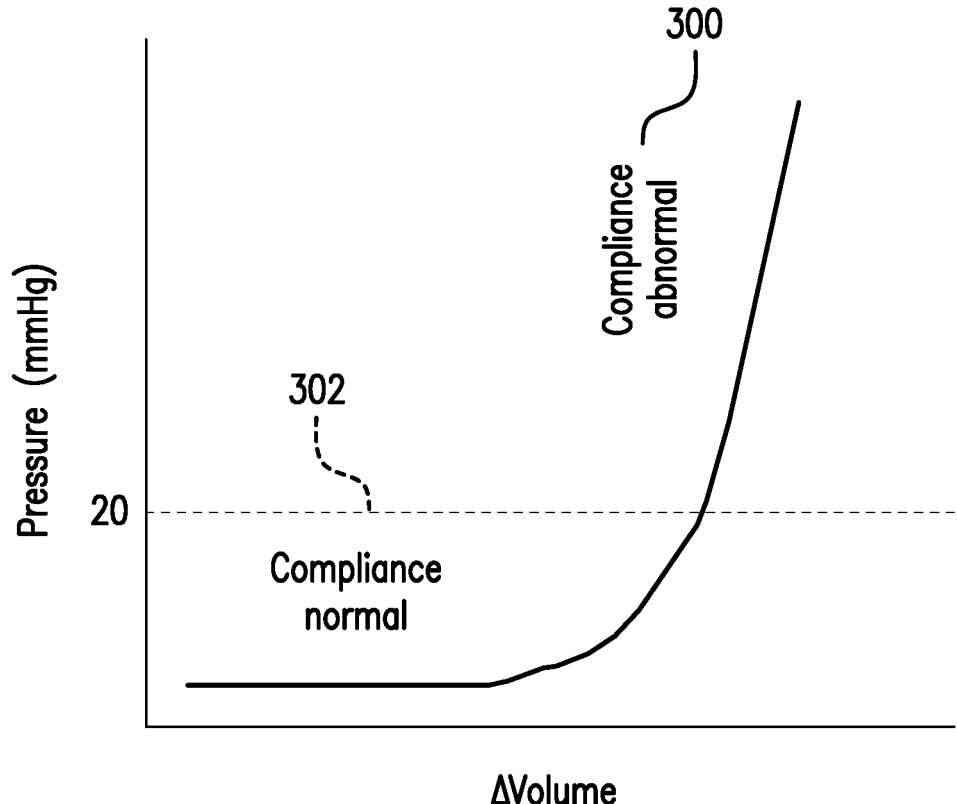
FIG. 3 is a diagram illustrating an exemplary compliance curve in accordance with the disclosed subject matter.

FIG. 3 is a diagram illustrating an exemplary compliance curve in accordance with the disclosed subject matter. The PCI can represent a correlation coefficient between the ICP and $ETCO_2$ across selected temporal epochs. The determination of PCI can leverage $CO_2$ cerebral blood vessel reactivity, where increases in partial pressure of $CO_2$ in arterial blood ($PaCO_2$) can produce predictable vasodilation and decrease produce predictable vasoconstriction, and temporal fluctuations in $PaCO_2$ due to normal respiratory variations. A linear relationship between the $PaCO_2$ and cerebral blood volume (CBV) can be utilized. For example and not limitation, a change in the $PaCO_2$ of 1 mmHg cam yield an approximately 2-7% change in cerebral blood flow (CBF) with a subsequent 0.9% to 2.4% approximate change in CBV that is related to changes in arterial CBV without changes in venous or capillary CBV. Since the CBF can be proportional to blood vessel radius to the fourth power under the Hagen-Poiseuille law, changes in the CBF can reflect immediate or recent changes in the CBV. Furthermore, the CBV can represent approximately 4.5% of total intracranial volume, and as such, intracranial volume can change by approximately 0.1-0.3% for every 1 mmHg change in the $PaCO_2$. The PCI can be considered normal, at 302, for example when an incremental change in the CBV results in no change in the $PaCO_2$. The PCI can be considered poor, at 300, for example when there is a correlation between an incremental change in CBV and a resulting change in the $PaCO_2$.

Figures 4A, 4B, 4C, 4D:
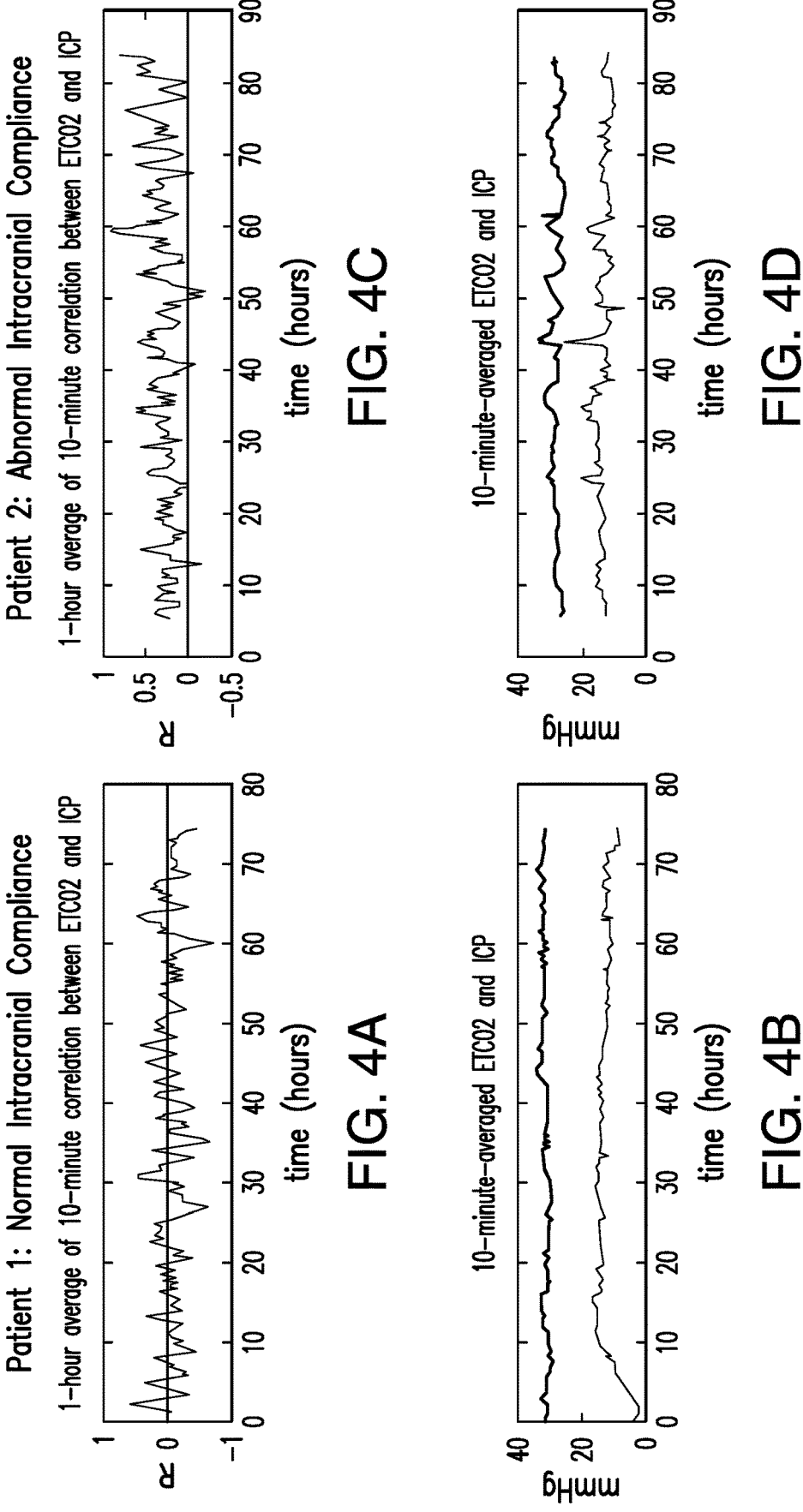
FIGS. 4A-4D are diagrams illustrating exemplary intracranial compliance determined from intracranial pressure and end tidal $CO_2$ measurements from a first representative patient (FIGS. 4A-4B) and a second representative patient (FIGS. 4C-4D) in accordance with the disclosed subject matter.
Figure 5A:
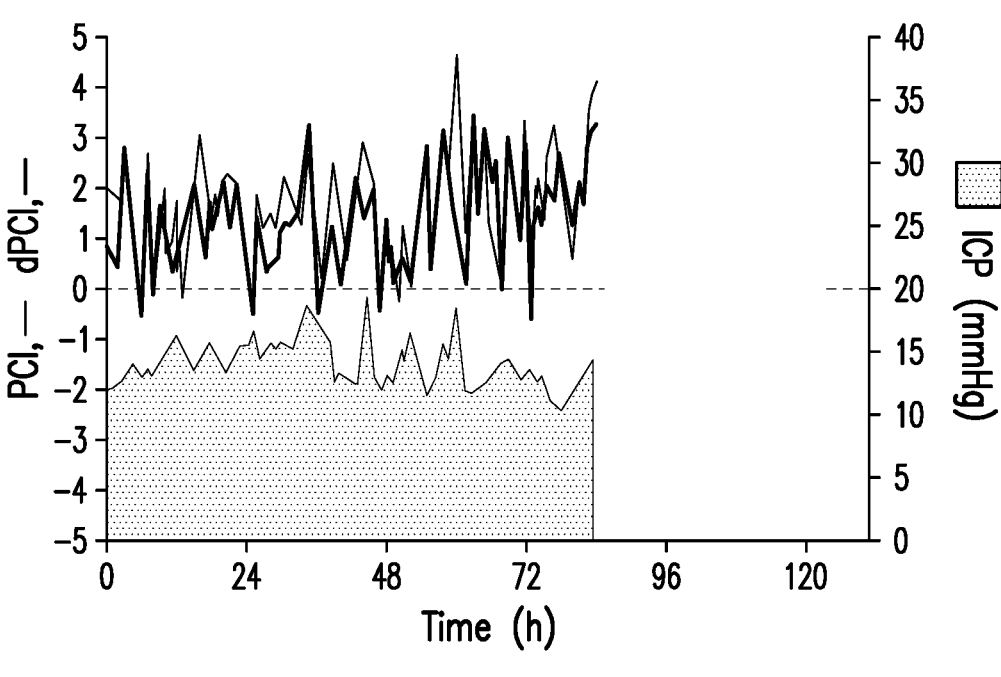
FIGS. 5A-5E are diagrams illustrating exemplary intracranial compliance determined from additional representative patients in accordance with the disclosed subject matter.
Figure 5B:
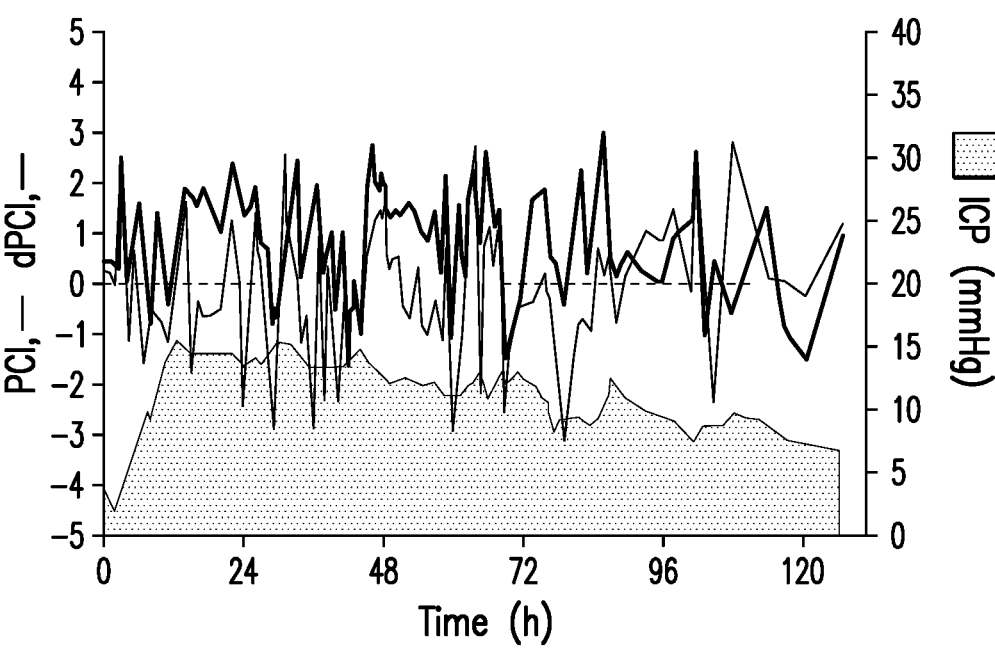
Figure 5C:
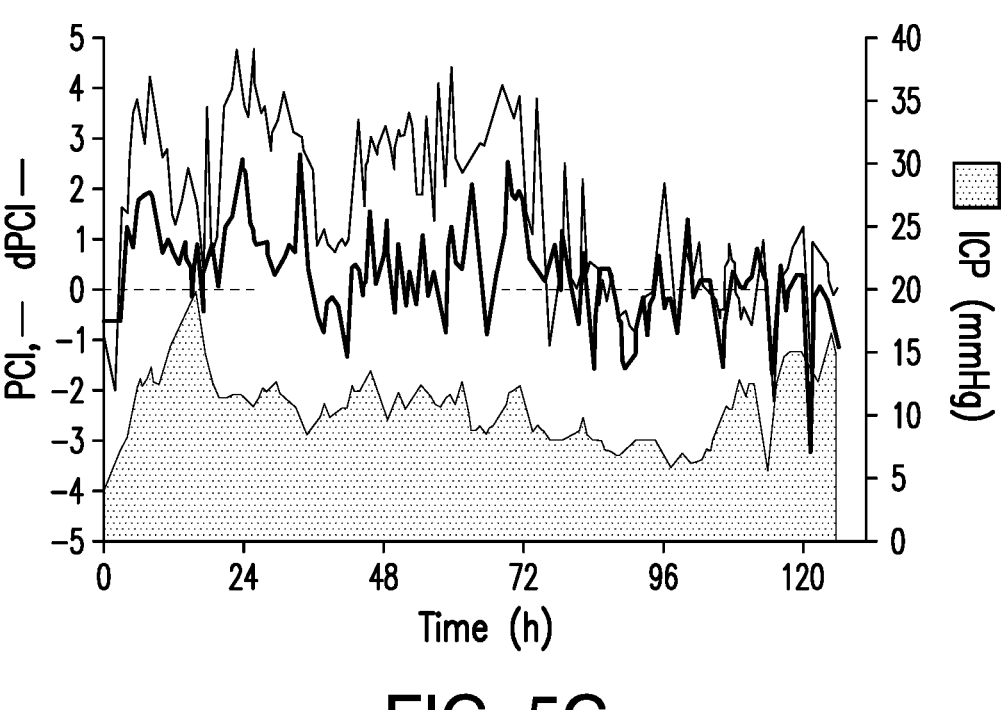
Figure 5D:
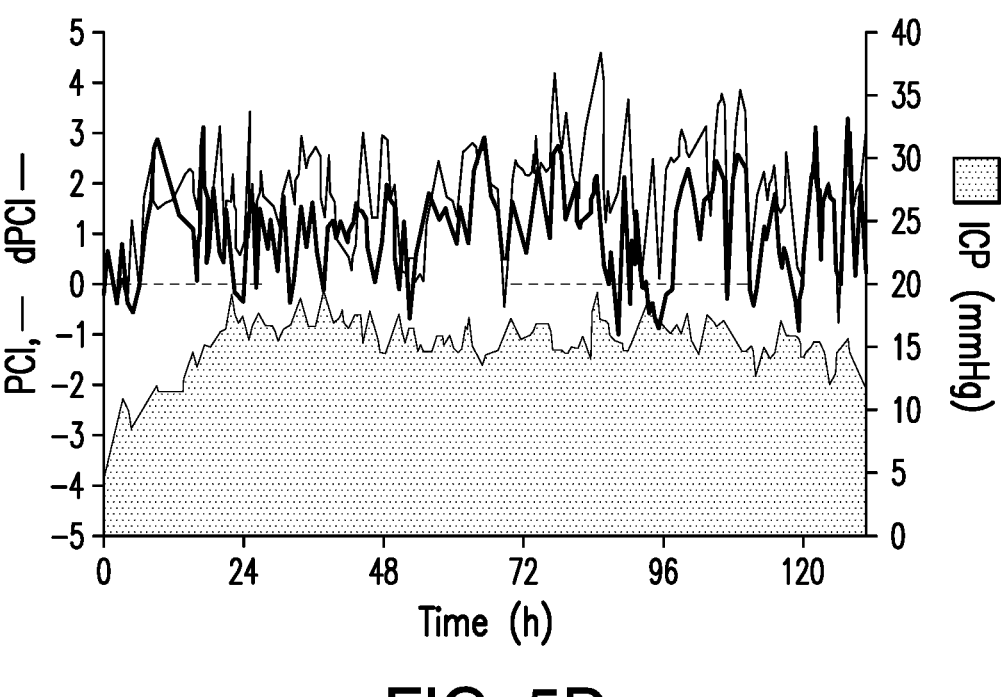
Figure 5E:
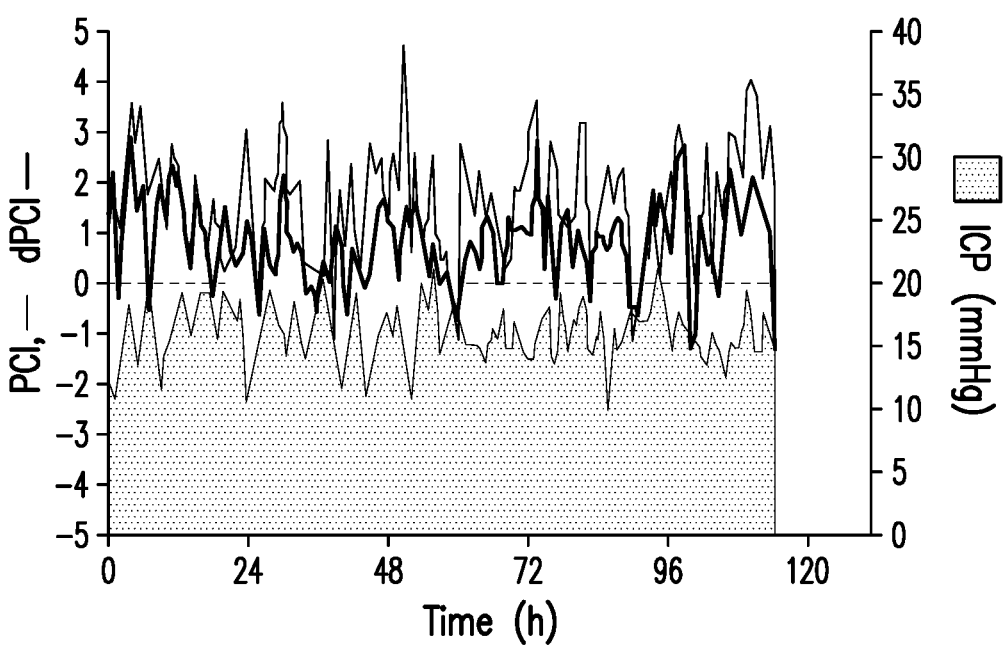

FIGS. 4A-4D are diagrams illustrating exemplary PCI determined from intracranial pressure and end tidal $CO_2$ measurements from a first representative patient (FIGS. 4A-4B) and a second representative patient (FIGS. 4C-4D) in accordance with the disclosed subject matter. In FIGS. 4A-4B, ICP and $ETCO_2$ show low level or absence of correlation over time indicating normal compliance and illustrated as a low PCI. In FIGS. 4C-4D, ICP and $ETCO_2$ show strong correlation over time indicating abnormal compliance and illustrated as a high PCI. For purpose of illustration and comparison, FIGS. 5A-5E are diagrams of PCI in five patients. FIGS. 5A, 5D, and 5E represent patients with consistently poor compliance, illustrated by high levels of PCI. FIG. 5B represents a patient with consistently normal compliance, illustrated by low levels of PCI. FIG. 5C represents a patient with initially poor compliance that becomes normal over time, illustrated by PCI that transitions from high to low levels over time. In FIGS. 5A-5E, for purpose of illustration and not limitation, as embodied herein, PCI is calculated as the direct correlation between ICP and $ETCO_2$ and rate-of-change between ICP and $ETCO_2$.

Figure 6A:
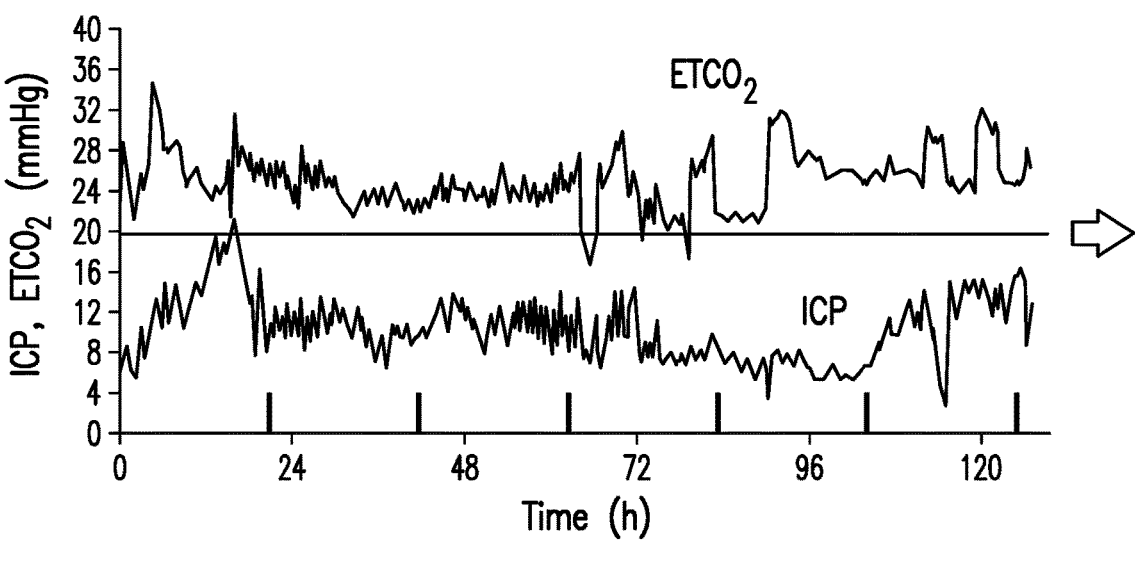
FIGS. 6A-6B are diagrams illustrating exemplary intracranial pressure and exemplary end tidal $CO_2$ used to determine intracranial compliance (FIG. 6A) and to predict responses to therapies (FIG. 6B) in accordance with the disclosed subject matter.
Figure 6B:
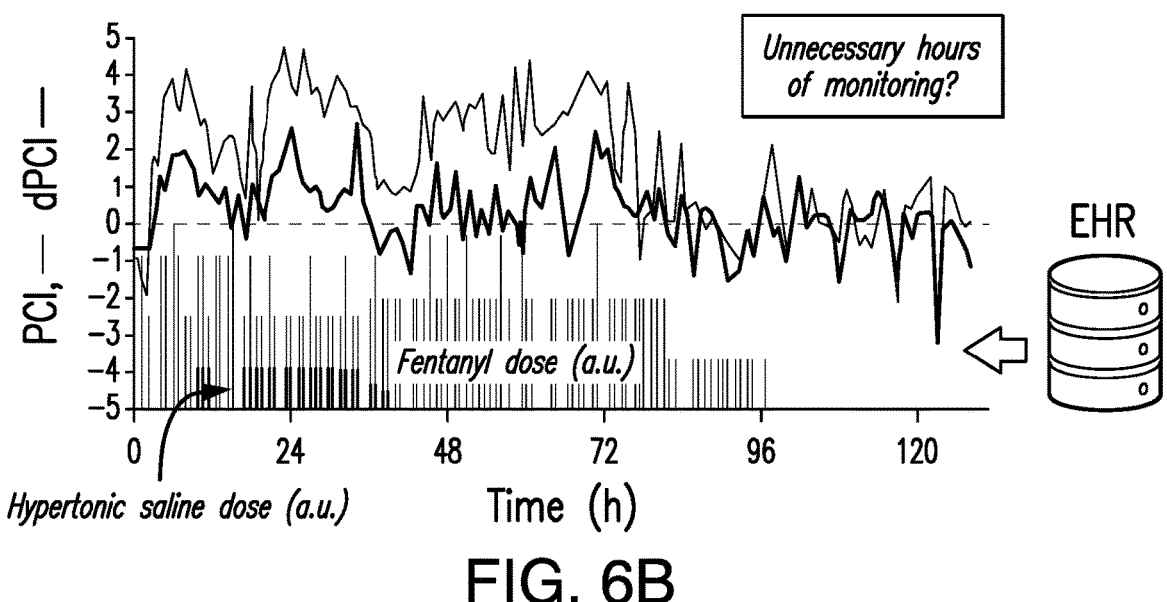

FIGS. 6A-6B are diagrams illustrating exemplary intracranial pressure and exemplary end tidal $CO_2$ used to generate estimates of PCI (FIG. 6A) and to predict responses to therapies (FIG. 6B). The PCI can predict a response of the patient to one or more therapies. For example, the PCI can be integrated and time-synchronized with electronic health record data to model predicted responses to one or more therapies. The one or more therapies can include hyperosmolar therapies such as hypertonic saline, or mannitol; use of sedative medications such as opioids, barbiturates, benzodiazepines, Propofol, or ketamine; drug-induced coma; therapeutic hypothermia; modification of minute ventilation $CO_2$ target; modification of blood pressure target; diversion of cerebrospinal fluid; or surgical decompression. A therapy can be selected based on the predicted response of the patient to the one or more therapies as determined by knowledge of PCI and electronic health record data.

With continued reference to FIGS. 6A-6B, knowledge of ICP alone can be insufficient to predict the need for therapies of fentanyl and hypertonic saline used for management of TBI, and/or the response to these therapies, as shown by an ICP that remains below the standard of care target threshold of 20 mmHg during the monitoring period (FIG. 6A). In contrast, knowledge of PCI can predict the need for therapies of fentanyl and hypertonic saline used for management of TBI, and the response to these therapies, as shown by normalization of PCI over time during the monitoring period (FIG. 6B). Knowledge of PCI in real time can allow or assist a clinician to select therapies proactively based on changes in PCI over time, rather than reactively in response to dangerous elevations in ICP.

Exemplary processors, such as processors 208, 258 described herein, can perform the techniques described herein, for example and not limitation, by executing software embodied in one or more tangible, computer-readable media, such as a memory unit. The memory unit can read the software from one or more other computer-readable media, such as a mass storage device or from one or more other sources via a communication interface. The software can cause the processor to execute the particular analysis or response process or particular processes including defining data structures stored in the memory unit and modifying such data structures according to the processes defined by the software. The processor can receive data from one or more input devices described herein, for example and not limitation, the intracranial pressure sensor 202 and the end tidal $CO_2$ sensor 204. The processor can communicate with one or more output interfaces described herein, such as a display or other user interface 210, a therapy module 260, a data acquisition system, an electronic health record system, or any other suitable output interface.

EXAMPLES

As an example, for purpose of illustration and confirmation of the disclosed subject matter, ICP was measured continuously with a surgically placed Codman microsensor (Integra Life Sciences, Plainsville, NJ, USA) and $ETCO_2$ with a CAPNOSTAT 5 sensor (Respironics, Murraysville, PA, USA) in line with the patient's ventilator. These devices were connected to a General Electric Solar 80001 clinical monitor (GE Healthcare, Chicago, IL, USA). Data was temporarily stored on a separate server using BedMaster Ex (Excel Medical, Jupiter, FL, USA) software for remote viewing and quality assurance review of patient data. No interventions were performed; for example, minute ventilation was not manipulated to provoke changes in patient $PaCO_2$ or $ETCO_2$ for the purposes of data collection.

ETCO$_2$ and ICP were collected every 5 seconds and archived. Software was developed to analyze archived time series data using MATLAB (MathWorks, Natick, MA, USA) as described herein. ETCO$_2$ and ICP values were sampled at 5 second intervals and filtered to remove artifacts, including absent values at a given time point that represent monitor malfunction or disconnection, ICP values <0, and ICP or ETCO$_2$ values >80 mmHg. Signals were smoothed by computation of a local mean representing one-minute windows advancing by 5 seconds per point. The 5 second interval data were converted to 1-minute mean ETCO$_2$ and ICP, and minute-to-minute delta ETCO$_2$ and delta ICP values. The Pearson's correlation coefficient was computed between 60 minutes of synchronous ETCO$_2$ and ICP values for the duration of the monitoring time. The subarachnoid hemorrhage (62.5%) and/or subdural hematoma (50%), with 37.5% of the patients having midline shift on initial head computed tomography (CT). Six of eight patients underwent decompressive surgery for relief of mass effect due to hemorrhage early after hospital admission and often prior to PICU admission and with ICP monitor placement occurring in the operating room (Patients 1, 3, 4, and 7). Patients 2 and 8 underwent decompressive surgery at 3 and 5 hours after hospital admission, respectively. As such, decompressive surgery occurred before data collection for determination of PCI in all patients. All patients survived to hospital discharge with 7 of 8 discharged to an inpatient rehabilitation facility.

TABLE 1

| Clinical Characteristics | | | | | | | | | |
|---|---|---|---|---|---|---|---|---|---|
| Patient | Age | Sex | GCS Initial | Mechanism of Injury | Surgical Intervention | ICP Monitor Days | ICU LOS (d) | Hospital LOS (d) | Discharge GCS |
| 1 | 15 y | M | 3 | MVC | DC | 6 | 27 | 31 | 15 |
| 2 | 14 y | M | 7T | Struck by debris | DC | 10 | 24 | 27 | 11 |
| 3 | 10 mo | F | 3T | Abusive head trauma | DC | 7 | 13 | 31 | 12 |
| 4 | 23 mo | M | 3T | GSW | DC | 6 | 9 | 12 | 15 |
| 5 | 2 y | F | 3T | GSW | None | 6 | 15 | 40 | 12 |
| 6 | 3 y | M | 6 | MVC | None | 8 | 11 | 20 | 15 |
| 7 | 7 y | M | 3T | Pedestrian struck by car | DC | 7 | 10 | 22 | 15 |
| 8 | 10 y | M | 3T | MVC | DC | 7 | 20 | 24 | 7 |

Abbreviations: F, female; GCS, Glasgow Coma Scale score; GSW, gunshot wound; ICP, intracranial pressure; LOS, length of stay; M, male; MVC, motor vehicle collision; T, tracheally intubated.

Figure 7A:
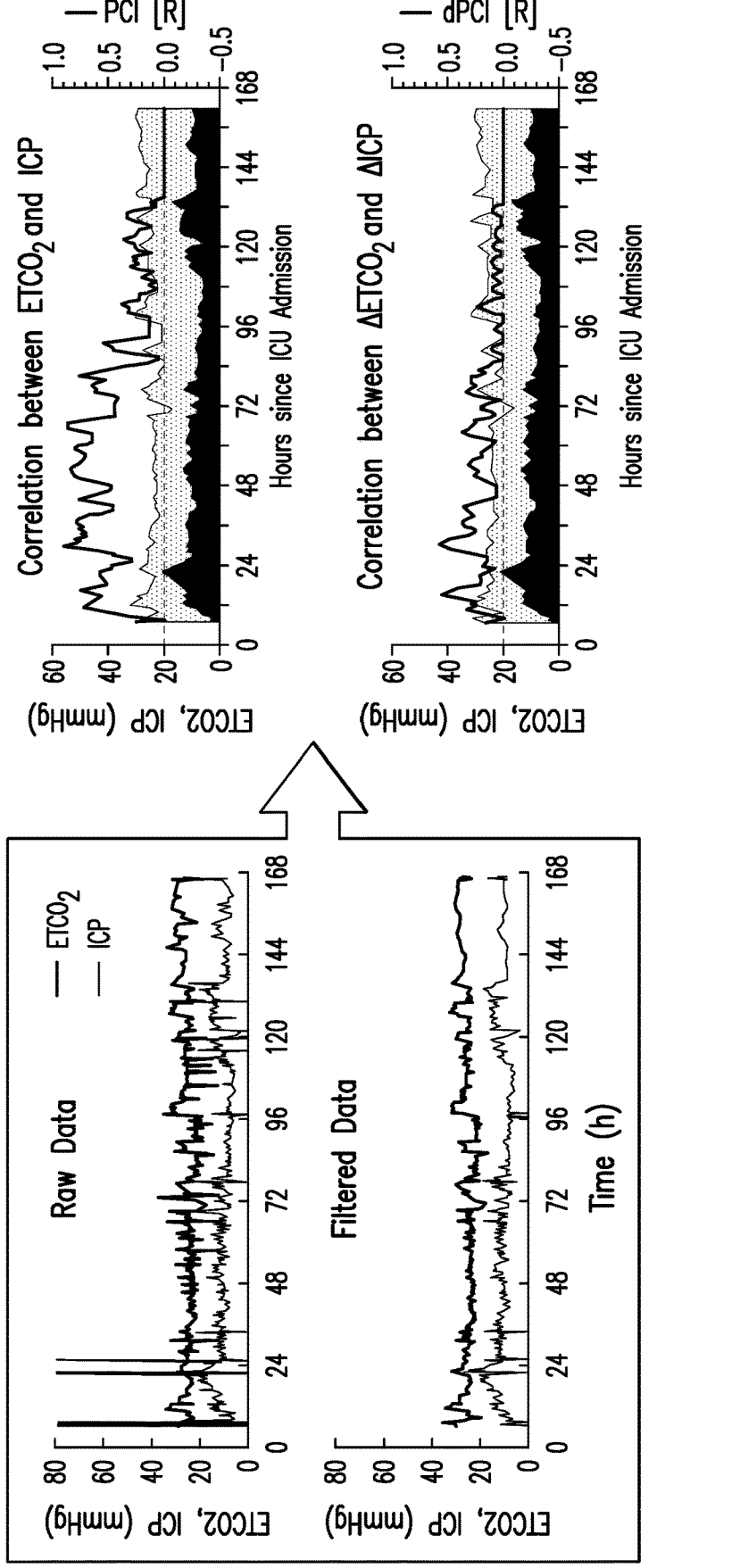
FIGS. 7A-7B are diagrams illustrating raw intracranial pressure and end tidal $CO_2$ monitor data over 5-second intervals before and after filtering and smoothing, and exemplary intracranial compliance calculations for purpose of illustration and confirmation of the disclosed subject matter.

Pearson's correlations were smoothed to reveal periodic trends. The resulting smoothed correlations defined the PCI, an index representing the Pearson's correlation coefficient between ETCO$_2$ and ICP or delta ETCO$_2$ and delta ICP. The equation used for calculating PCI is shown in FIG. 7A. Hour-to-hour variability was reduced when calculating the Pearson's correlation coefficient using delta ETCO$_2$/delta ICP vs. ETCO$_2$/ICP. As such, the correlation between the change in ETCO$_2$ and change in ICP was used for determination of PCI.

Data was presented as mean±standard deviation (SD) or median (interquartile range (IQR)) as appropriate. Hourly ICP, ETCO$_2$, and PCI data for individual patients were generated using Prism 7.0c (GraphPad Software, Inc., La Jolla, CA, USA). Hourly ICP, cerebral perfusion pressure, and PCI were pooled for all patients and fit to a smooth curve using local polynomial regression fitting with a span of 0.10. Curve fitting for pooled patient data was performed using the 'geom_smooth' function in the 'ggplot2' package in R (www.r-project.org and R studio, Boston, MA). The percentage of time dPCI was above thresholds of 0.1, 0.2, 0.3, 0.4, and 0.5 is presented as mean, median, 5, 25, 75, and 95$^{th}$ percentiles.

Demographic data from eight consecutive patients with continuous ICP and ETCO$_2$ monitoring as part of the management of severe TBI are shown in Table 1. The mean age was 7.1±5.8 years (range 10 months-15 years), average monitor days 7.1±1.4, average PICU length of stay (LOS) 16.1±6.8 days, and average hospital LOS 25.9±8.4 days. Most patients had intraparenchymal, intraventricular or PCI was calculated from 978 hours of ETCO$_2$ and ICP monitoring (122±33 hours/patient). FIG. 7A shows the raw ICP and ETCO$_2$ monitor data, plotted at 5-second intervals before and after filtering and smoothing, and PCI calculations from Patient 3. Hourly ICP, ETCO$_2$, and PCI data for all patients are provided in FIG. 7B (for all patients, time is displayed as hours since ICU admission).

Figure 7B:
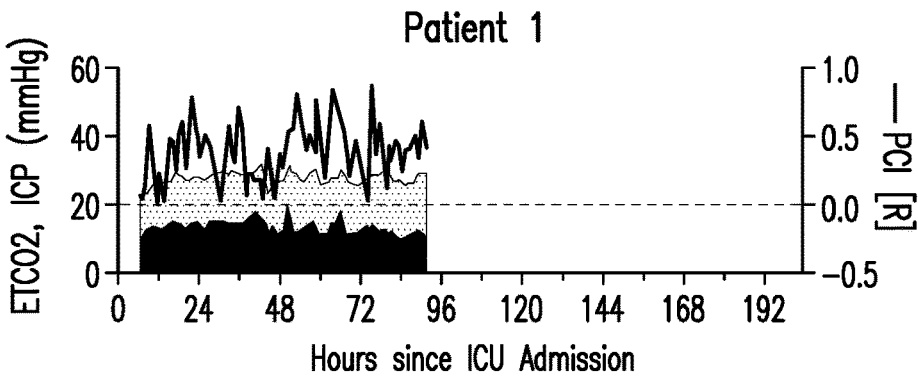
Figure 7B:
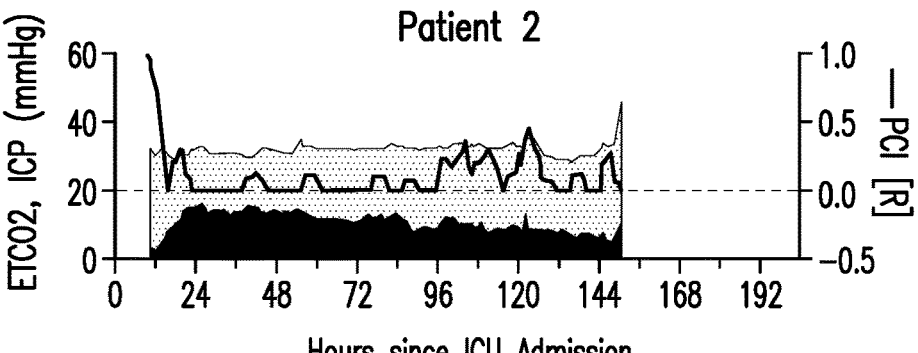
Figure 7B:
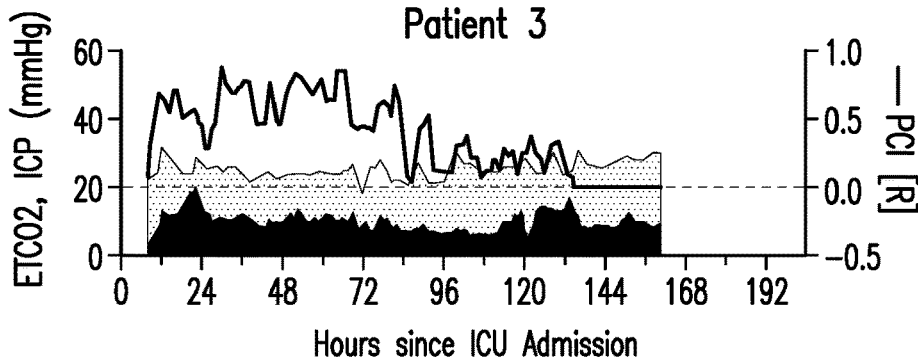
Figure 7B:
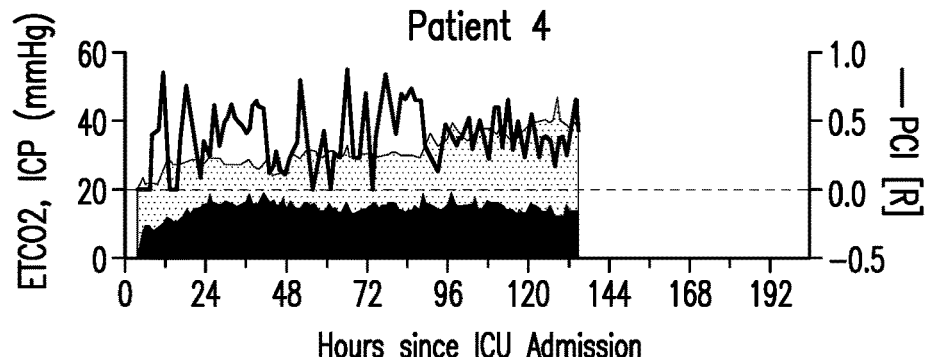
Figure 7B:
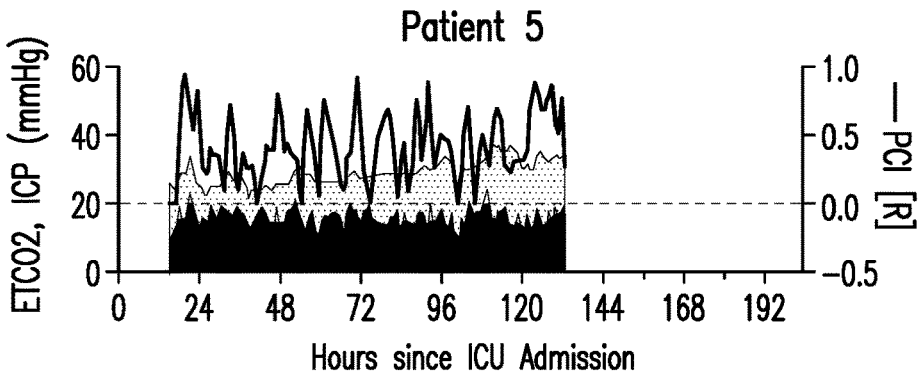
Figure 7B:
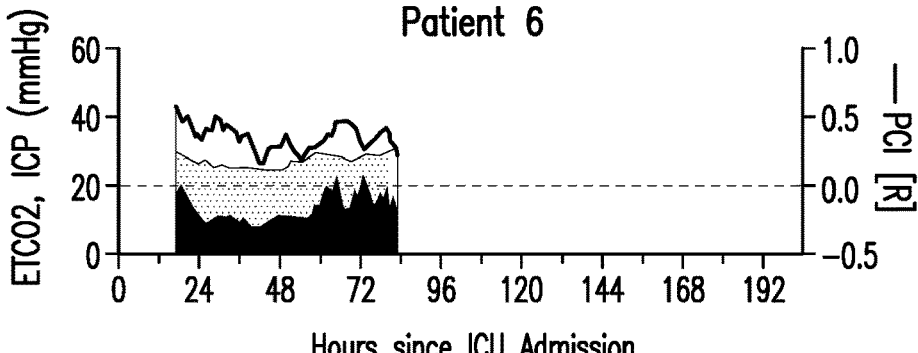
Figure 7B:
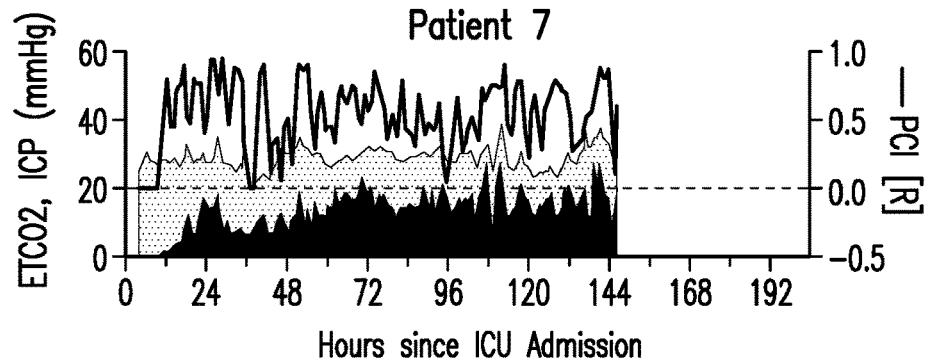
Figure 7B:
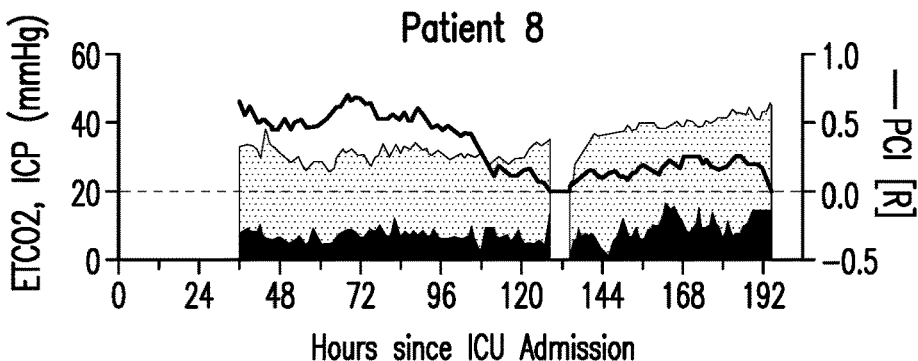
Figure 7B:
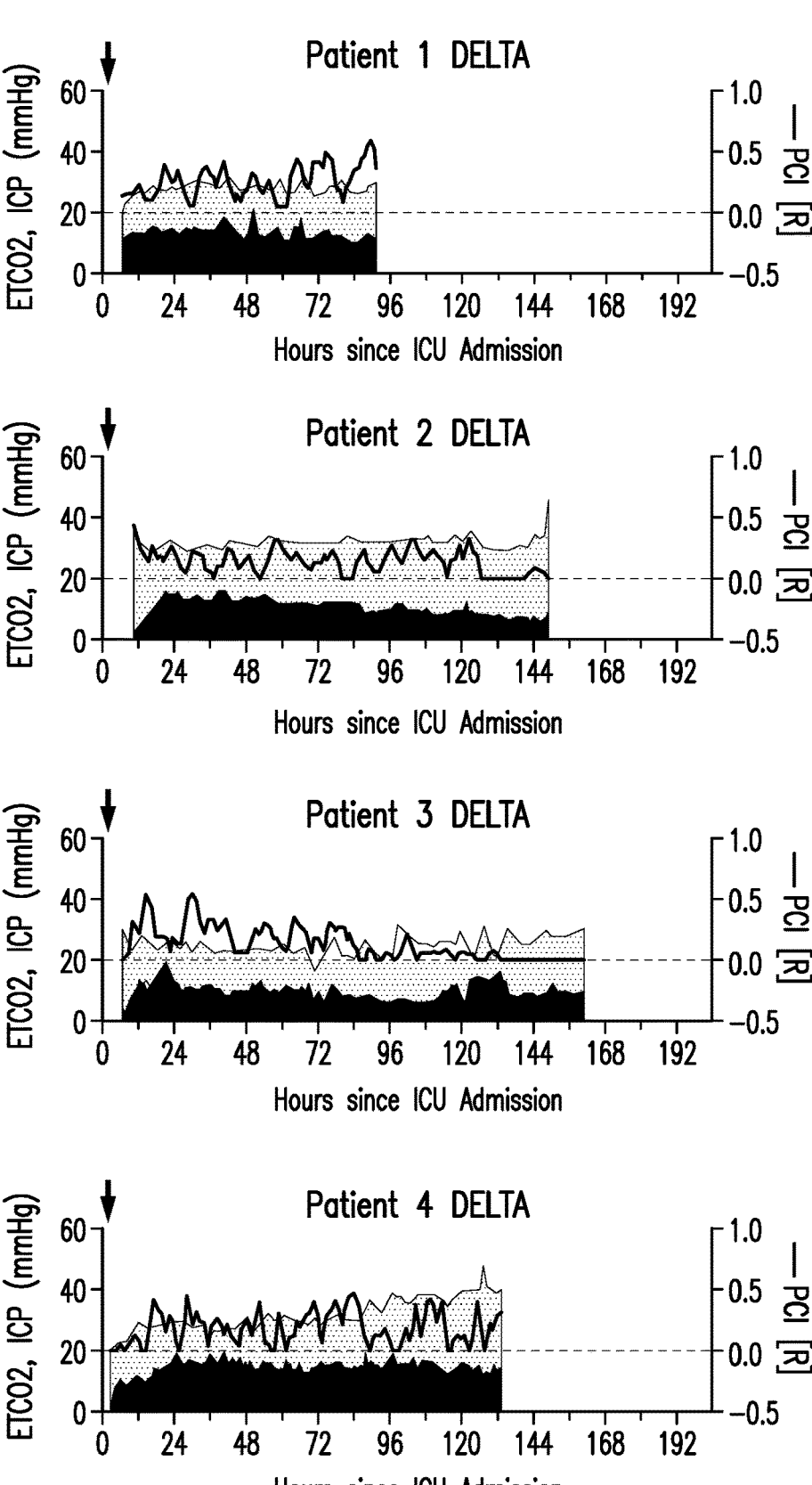
Figure 7B:
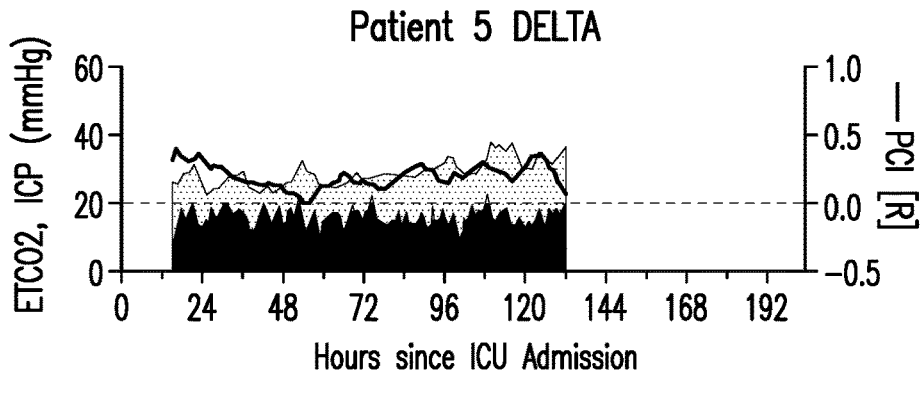
Figure 7B:
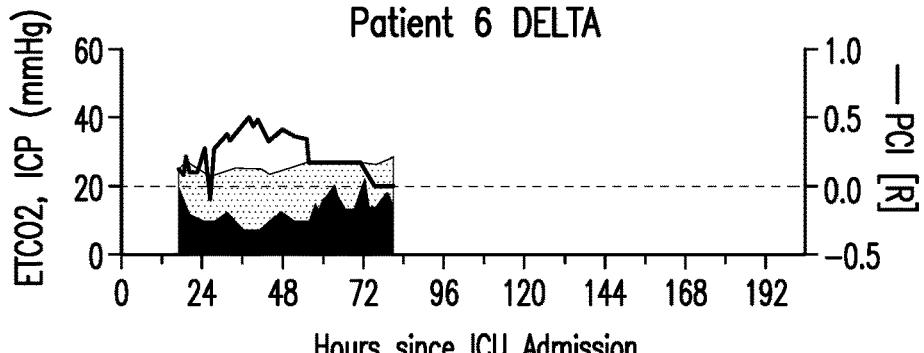
Figure 7B:
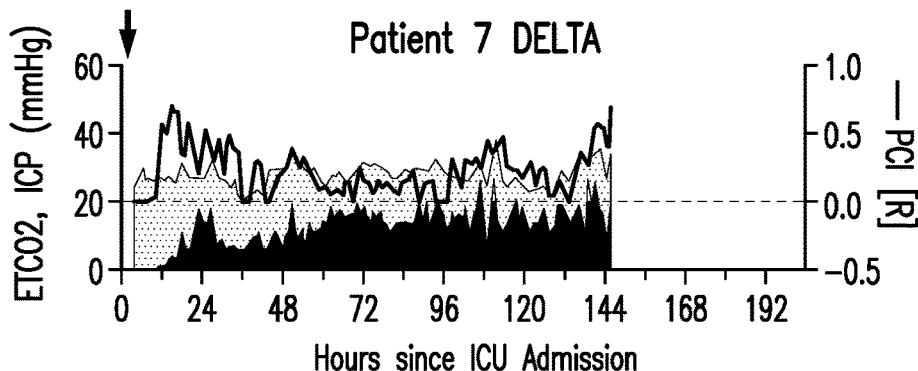
Figure 7B:
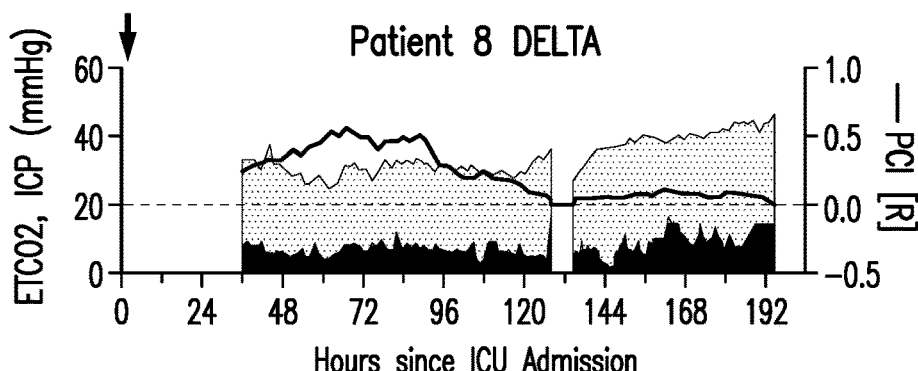

FIGS. 7A-7B depict PCI with continuous ICP and ETCO$_2$ monitoring. Raw data signals were captured from GE Solar 80001 clinical monitors and exported to BedMaster Ex. Raw data was filtered to remove nonsensical data and moment-to-moment correlations between ETCO$_2$ and ICP, and ΔETCO$_2$ and ΔICP are calculated using MATLAB, where $X_a$ is a matrix of ETCO$_2$ (or ΔETCO$_2$) and $Y_b$ is a matrix of ICP (or ΔICP) values. Correlations were binned into 1-hour epochs (n=60) to derive PCI. For purpose of illustration and not limitation, as embodied herein "good compliance" can be identified by a lack of correlation between ETCO$_2$ (gray) and ICP (black), or a PCI~0, and "poor compliance" can be identified by a positive correlation between ETCO$_2$ and ICP and/or changes in ETCO$_2$ and ICP over time, or a PCI>0.18. As shown in FIG. 7A, a patient with a PCI>0.18 improved over time (Patient 3). FIG. 7B shows individual data from all 8 patients. Block arrows represent time of surgical decompression (if applicable).

Determining the correlation between ETCO$_2$ and ICP demonstrated substantially more variability than determining the correlation between the change in ETCO$_2$ and the corresponding change in ICP, and as such, PCI determined using changes in ETCO$_2$ and changes in ICP was evaluated in this patient cohort. The mean PCI across each patient's entire ICP monitoring period is shown in Table 2. The average PCI for all patients was 0.18±0.04, whereas the average ICP for all patients was 13.0±2.8 mmHg. Several temporal patterns were observed, including PCI≤0.18 (cohort mean) throughout the majority of the monitoring period; PCI>0.18 throughout the majority of the monitoring period; and PCI>0.18 initially that resolved later during the monitoring period.

TABLE 2

Mean PCI and ICP for Individual Patients

| Patient | Captured monitor time (h) | Mean PCI | Mean ICP (mmHg) |
|---|---|---|---|
| 1 | 85 | 0.24 | 14 |
| 2 | 141 | 0.11 | 12 |
| 3 | 125 | 0.12 | 11 |
| 4 | 132 | 0.18 | 15 |
| 5 | 119 | 0.18 | 17 |
| 6 | 66 | 0.19 | 14 |
| 7 | 139 | 0.23 | 14 |
| 8 | 171 | 0.18 | 8 |
| All patients | 122 ± 33 | 0.18 ± 0.04 | 13 3 |

Figure 8A:
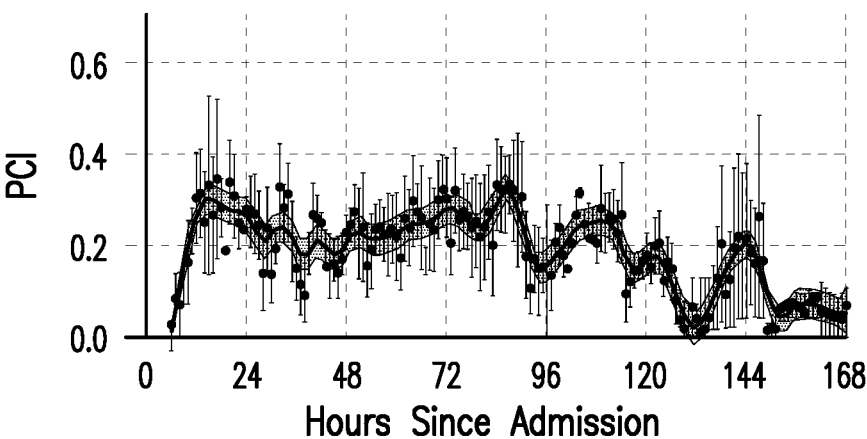
FIGS. 8A-8B are diagrams illustrating measurement data for eight exemplary patients including a temporal pattern for intracranial compliance, intracranial pressure, and cerebral perfusion pressure for purpose of illustration and confirmation of the disclosed subject matter.
Figure 8A:
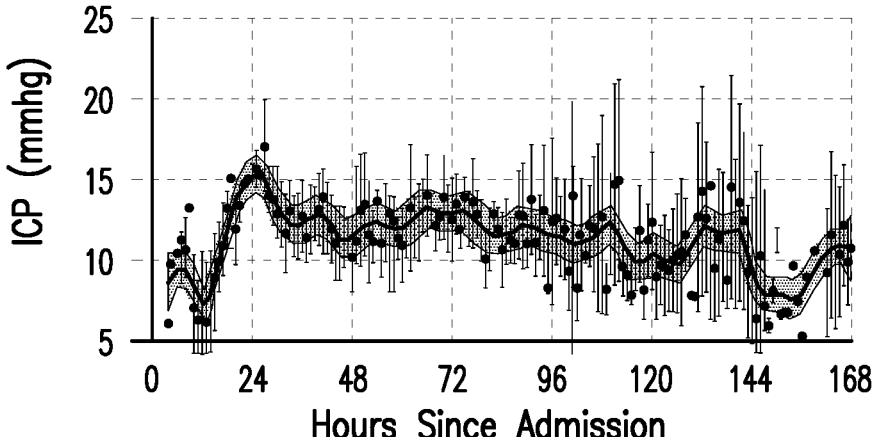
Figure 8A:
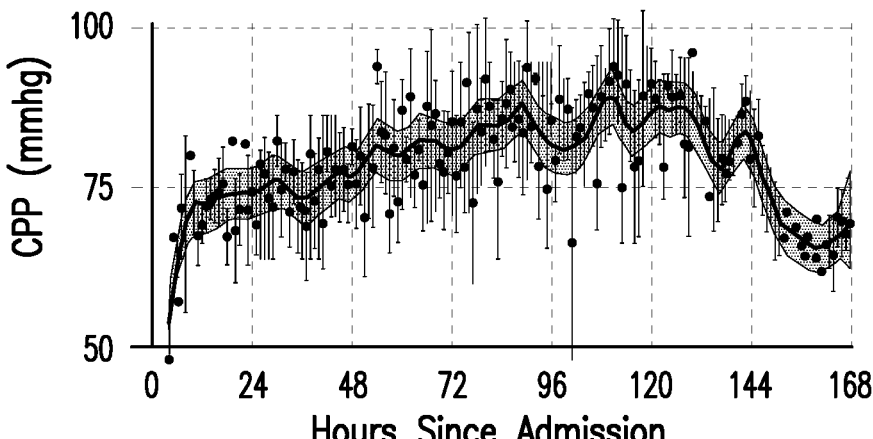
Figure 8B:
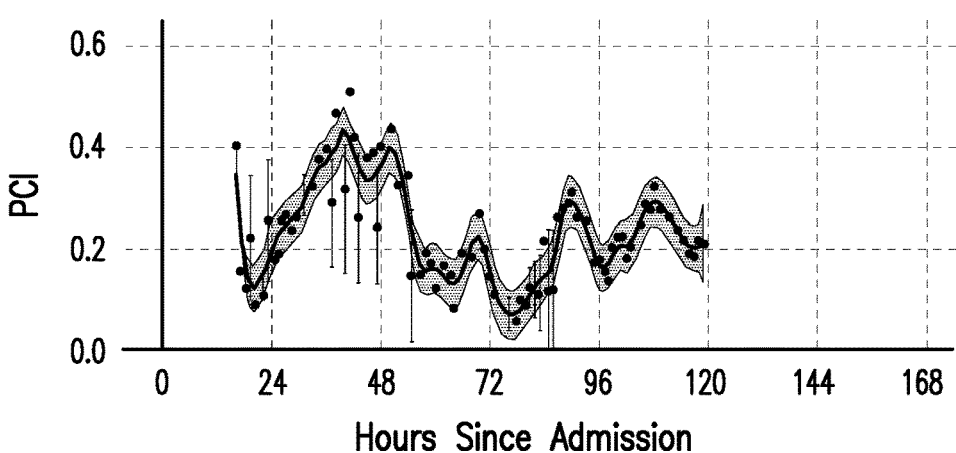
Figure 8B:
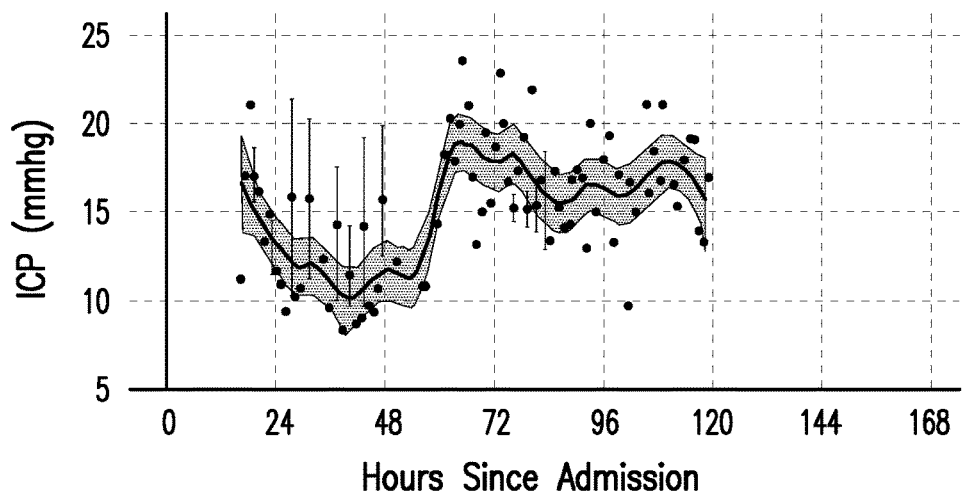
Figure 8B:
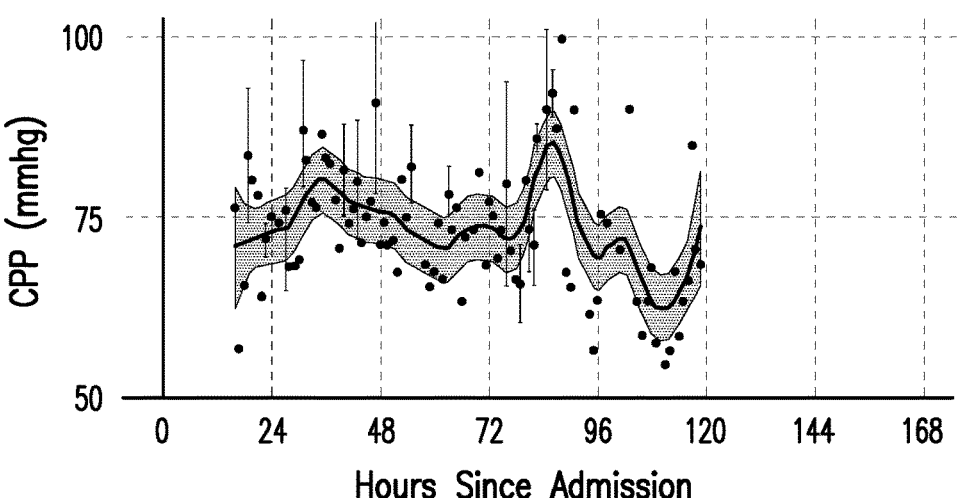
Figure 8B:
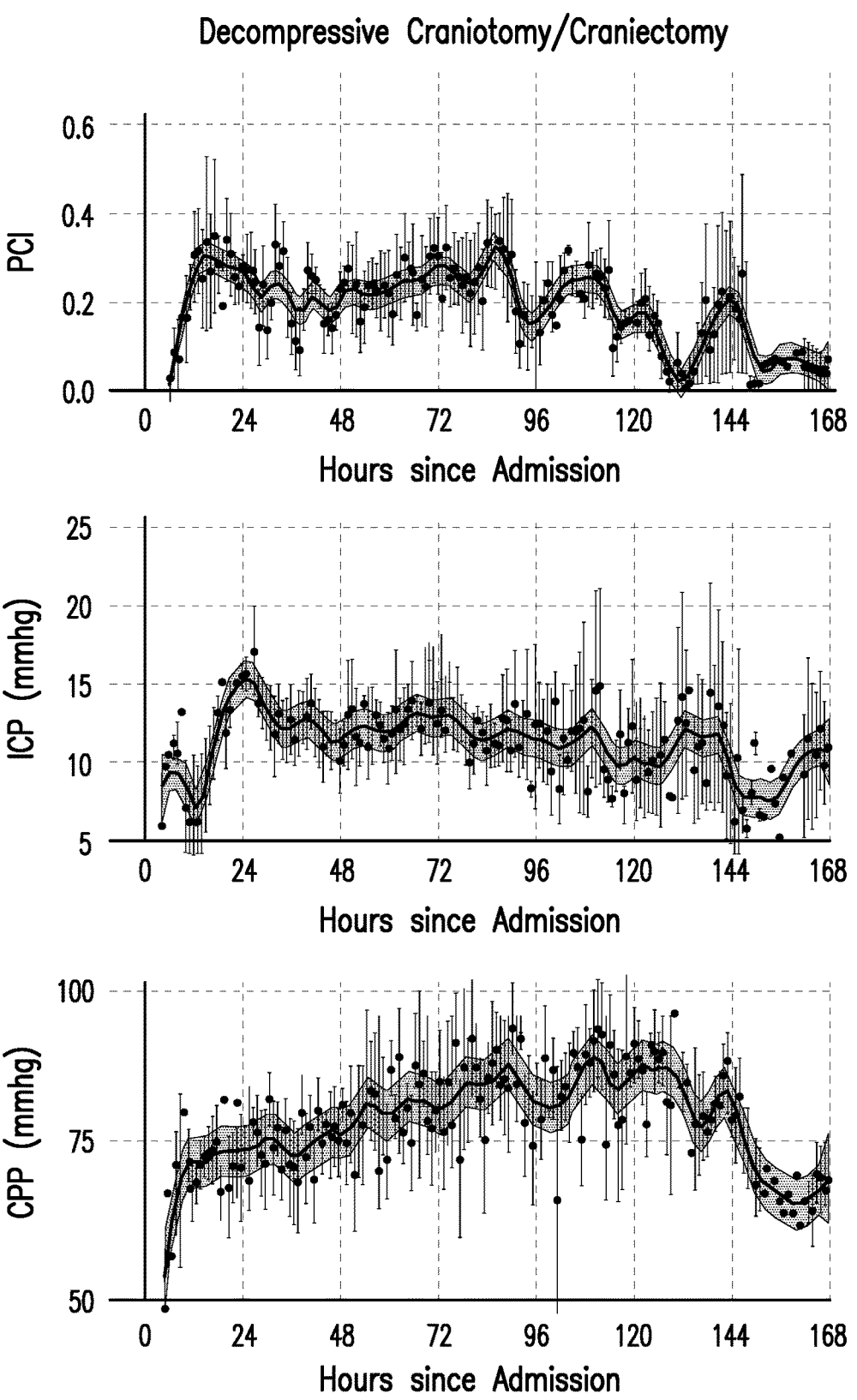

Aggregate data for all patients (n=8) showing the temporal pattern for PCI, ICP, and CPP are provided in FIG. 8A. In this cohort, PCI increased over the first 12 hours after admission. The majority of PCI values remained above 0.18 until ~90 hours after admission. In contrast, aggregate ICP in this cohort remained consistently below the treatment threshold of 20 mmHg throughout the monitoring period. Aggregate temporal data are also provided for patients that did (n=6) or did not (n=2) undergo surgical decompression in FIG. 8B, showing some temporal differences in PCI and ICP between groups.

Figure 9:
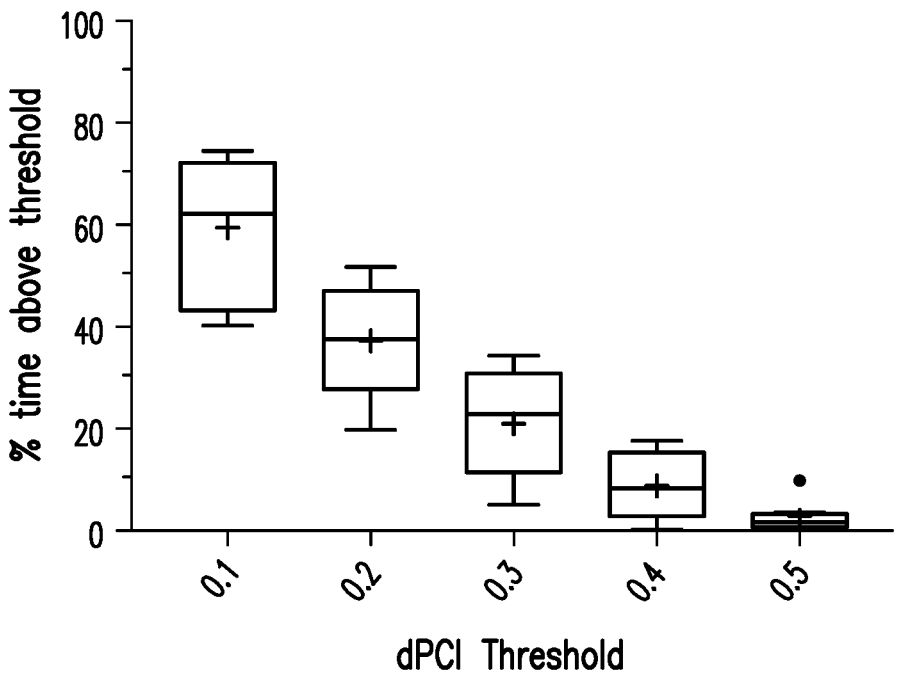
FIG. 9 are diagrams illustrating intracranial compliance above a threshold over time for eight exemplary patients for purpose of illustration and confirmation of the disclosed subject matter.

Percent time PCI is above threshold for all patients is shown in FIG. 9. The percentage of time spent with a PCI threshold >0.1, 0.2, 0.3, 0.4, and 0.5 was 62.0% [24.3], 37.5% [13.7], 22.5% [14.7], 7.9% [12.1], and 1.4% [3.2], respectively. The percentage of time spent with an ICP threshold >20 mmHg was 5.1% [14.6].

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

14

What is claimed is:

1. A method for monitoring intracranial compliance in a patient comprising:
obtaining, by a processor, a measurement indicative of an intracranial pressure of a patient from an intracranial pressure sensor configured to be implanted in or disposed proximate a skull of the patient;
obtaining, by a processor, a measurement indicative of a $CO_2$ level of the patient from an end tidal $CO_2$ sensor or a partial pressure of $CO_2$ sensor, wherein the end tidal $CO_2$ sensor or the partial pressure of $CO_2$ sensor is configured to be disposed in an endotracheal tube or a transcutaneous or indwelling vascular catheter;
determining an intracranial compliance from the measurement indicative of the intracranial pressure and the measurement indicative of the $CO_2$ level of the patient with the processor, wherein the processor is coupled to or in communication with the intracranial pressure sensor and the end tidal $CO_2$ sensor or a partial pressure of $CO_2$ sensor, wherein the intracranial compliance is determined based on a correlation coefficient of the measurement indicative of the intracranial pressure and the measurement indicative of the $CO_2$ level;
determining a therapy based on the intracranial compliance; and
administering the therapy to the patient, wherein the therapy includes at least one of hypertonic saline, mannitol, opioids, barbiturates, benzodiazepines, Propofol, ketamine, drug-induced coma, therapeutic hypothermia, modification of minute ventilation $CO_2$ target, modification of blood pressure target, diversion of cerebrospinal fluid, and surgical decompression.

2. The method of claim 1, wherein at least one of the measurements indicative of the intracranial pressure and the $CO_2$ level of the patient is obtained from a data acquisition platform.

3. The method of claim 1, wherein at least one of the measurements indicative of the intracranial pressure and the $CO_2$ level of the patient is obtained from an electronic health record.

4. The method of claim 1, wherein at least one of the measurements indicative of the intracranial pressure and the $CO_2$ level of the patient is obtained from a monitor for intensive care.

5. The method of claim 1, further comprising synchronizing the measurements indicative of the intracranial pressure and the $CO_2$ level of the patient.

6. The method of claim 1, further comprising at least one of providing the intracranial compliance to a user interface, providing an alert when the intracranial compliance exceeds a threshold indicating abnormal compliance, and providing the intracranial compliance to an electronic health record.

7. The method of claim 1, further comprising determining, by the processor, an updated intracranial compliance based on a change in at least one of the measurements indicative of the intracranial pressure and the $CO_2$ level of the patient in response to the therapy.

8. The method of claim 1, further comprising predicting, by the processor, a response of the patient to one or more determined therapies, wherein the therapy is selected based on the predicted response of the patient to the one or more determined therapies.

* * * * *